US00PP30466P2

(12) United States Plant Patent
Fitzgerald

(10) Patent No.: US PP30,466 P2
(45) Date of Patent: Apr. 30, 2019

(54) ***CAREX* PLANT NAMED 'EVERGLOW'**

(50) Latin Name: *Carex morrowii*
Varietal Denomination: Everglow

(71) Applicant: Pat Fitzgerald, Kilkenny (IE)

(72) Inventor: Pat Fitzgerald, Kilkenny (IE)

(73) Assignee: GARRAITH LTD., Old Town, Stoneyford (IE)

( * ) Notice: Subject to any disclaimer, the term of this patent is extended or adjusted under 35 U.S.C. 154(b) by 0 days.

(21) Appl. No.: 15/732,710

(22) Filed: Dec. 18, 2017

(30) Foreign Application Priority Data

Nov. 24, 2017 (QZ) ..... PBR 20173088

(51) Int. Cl.
*A01H 5/12* (2018.01)

(52) U.S. Cl.
USPC ..... Plt./384

(58) Field of Classification Search
USPC ..... Plt./384
See application file for complete search history.

*Primary Examiner* — Keith O. Robinson
(74) *Attorney, Agent, or Firm* — Penny J. Aguirre

(57) ABSTRACT

A new cultivar of *Carex oshimensis*, 'Everglow', characterized by its variegated foliage with green centers and creamy white and light orange margins and its an upright plant habit.

2 Drawing Sheets

Botanical classification: *Carex morrowii.*
Varietal denomination: 'Everglow'.

BACKGROUND OF THE INVENTION

The present invention relates to a new and distinct cultivar of *Carex morrowii* and will be referred to hereafter by its cultivar name, 'Everglow'. 'Everglow' is a new cultivar of perennial ornamental grass grown for container and landscape use.

The new cultivar arose through an ongoing breeding and selection program conducted by the Inventor in Oldtown, Stoneyford, Co. Kilkenny, Republic of Ireland. The new cultivar arose from self crossing of *Carex morrowii* 'Fisher's Form' (not patented) in 2015. The Inventor selected 'Everglow' as a single unique plant in 2016.

Asexual propagation of the new cultivar was first accomplished by tissue culture of meristem tissue by the Inventor in 2016 in Oldtown, Stoneyford, Co. Kilkenny, Republic of Ireland. Asexual propagation by tissue culture and division have determined that the characteristics are stable and are reproduced true to type in successive generations.

SUMMARY OF THE INVENTION

The following traits have been repeatedly observed and represent the characteristics of the new cultivar. These attributes in combination distinguish 'Everglow' as a distinct cultivar of *Carex*.

1. 'Everglow' exhibits variegated foliage with green centers and creamy white and light orange margins.
2. 'Everglow' exhibits an upright plant habit.

'Fisher's Form', the parent plant of 'Everglow', is similar to 'Everglow' in having an upright plant habit. 'Fisher's Form' differs from 'Everglow' in having variegated foliage with green centers and white margins. 'Everglow' can be most closely compared to *Carex morrowii* cultivars 'Ice Dance' (not patented) and 'Ice Ballet' (U.S. Plant Pat. No 20,228). Both 'Ice Dance' and 'Ice Ballet' differ from 'Everglow' in having variegated foliage with green centers and white margins.

BRIEF DESCRIPTION OF THE DRAWINGS

The accompanying colored photographs illustrate the overall appearance and distinct characteristics of a six month-old plant of the new *Carex* as field grown outdoors in a 9-cm container in Oldtown, Stoneyford, Co. Kilkenny, Republic of Ireland.

The photograph in FIG. 1 illustrates the plant habit and appearance of 'Everglow'.

Figure 1:
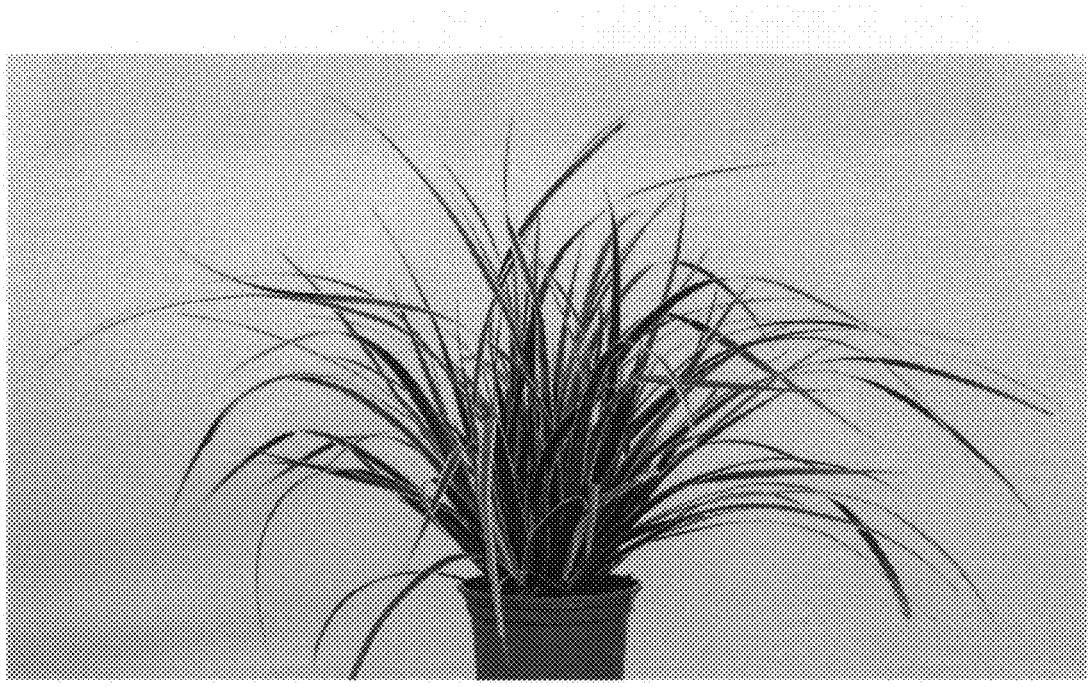
Figure 2:
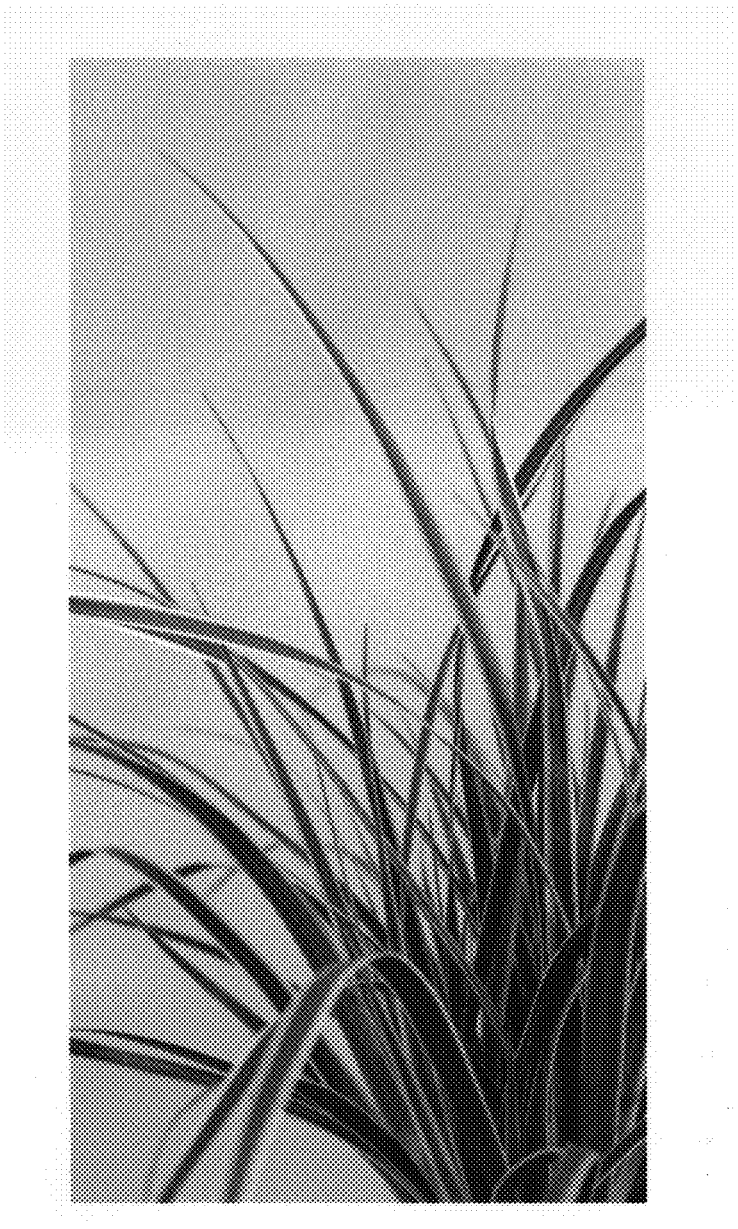

The photograph in FIG. 2 provides a close-up view of the foliage of 'Everglow'.

The colors in the photographs may differ slightly from the color values cited in the detailed botanical description, which accurately describe the colors of the new *Carex*.

DETAILED BOTANICAL DESCRIPTION

The following is a detailed description of six month-old plants of the new cultivar as grown outdoors in 9-cm containers in Oldtown, Stoneyford, Co. Kilkenny, Republic of Ireland. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant habit.*—Herbaceous perennial, flattened globular with arching leaves.

*Growth habit.*—Upright, compact, arching foliage.

*Height and spread.*—30 to 40 cm in height and 45 to 60 cm in diameter.

*Hardiness.*—At least in U.S.D.A. Zones 6 to 11.

*Diseases and pests*.—No susceptibility or resistance to pests and diseases has been oberved.

*Root description*.—Short, stout rhizomes with dense, fibrous roots, roots moderately branched.

*Propagation*.—Shoot division.

*Root development*.—A division will root in about 3 weeks and a young plant will fully root in a liner in about 12 weeks.

*Shoots*.—An average of 22 main shoots growing from the base, base of shoot is triangular in shape.

*Growth rate*.—Moderate.

Foliage description:

*Leaf shape*.—Linear, strongly curved.

*Leaf division*.—Simple.

*Leaf base*.—Sheathing.

*Leaf apex*.—Long acuminate.

*Leaf aspect*.—Average angle of 30° to shoot axis, leaves initially emerge upright, then cascade outward and finally arch downward.

*Leaf venation*.—Parallel, upper and lower surfaces 143C.

*Leaf margins*.—Entire and moderately sharp when rubbed downwards due to very small teeth too small to be seen or measured.

*Leaf size*.—Average of 30.9 cm in length and 8 mm in width.

*Leaf number*.—Average of 11 leaves per shoot.

*Leaf arrangement*.—Alternate.

*Leaf surface*.—Upper and lower surface smooth, glabrous, moderately glossy.

*Leaf color*.—Young upper and lower surface; 144A, margined 22A to 22B, mature upper surface; 137A, margined 24B, margins fading towards the tip to 145D, mature lower surface; 137C, margined 24B to 24C margins fading towards the tip to 153D.

*Petiole*.—None.

*Leave sheathes*.—Average of 2.6 cm in length, 6 mm in width, 177D and 200D.

Flower description: Flowers have not been observed.

It is claimed:

1. A new and distinct cultivar of *Carex* plant named 'Everglow' as herein illustrated and described.

* * * * *